US012727953B2

(12) United States Patent
Pocrnich et al.

(10) Patent No.: US 12,727,953 B2
(45) Date of Patent: Sep. 8, 2026

(54) STEERABLE TIP CATHETER WITH AUTOMATIC TENSION APPARATUS

(71) Applicant: Nextern Innovation, LLC, White Bear Lake, MN (US)

(72) Inventors: John Pocrnich, Roseville, MN (US); Steve Gigl, Crystal, MN (US); John Swoyer, Blaine, MN (US)

(73) Assignee: NEXTERN INNOVATION, LLC, White Bear Lake, MN (US)

( * ) Notice: Subject to any disclaimer, the term of this patent is extended or adjusted under 35 U.S.C. 154(b) by 1201 days.

(21) Appl. No.: 17/453,988

(22) Filed: Nov. 8, 2021

(65) Prior Publication Data

US 2022/0142725 A1 May 12, 2022

Related U.S. Application Data

(60) Provisional application No. 63/111,408, filed on Nov. 9, 2020.

(51) Int. Cl.
*A61B 34/00* (2016.01)
*A61B 34/30* (2016.01)
(Continued)

(52) U.S. Cl.
CPC .............. *A61B 34/71* (2016.02); *A61B 34/30* (2016.02); *A61B 34/76* (2016.02);
(Continued)

(58) Field of Classification Search
CPC ......... A61B 34/71; A61B 34/30; A61B 34/76; A61B 2034/301; A61B 2034/715;
(Continued)

(56) References Cited

U.S. PATENT DOCUMENTS 5,374,261 A 12/1994 Yoon
5,486,195 A 1/1996 Myers et al.
(Continued)

FOREIGN PATENT DOCUMENTS

CN 101918073 A 12/2010
CN 103379853 A 10/2013
(Continued)

OTHER PUBLICATIONS

A. A. Adib et al., "Direct-write 3D printing and characterization of a GelMA-based biomaterial for intracorporeal tissue engineering," Biofabrication, vol. 12, No. 4, Art. No. 4, Jul. 2020, doi: 10.1088/1758-5090/ab97a1.

(Continued)

*Primary Examiner* — Adam J Eiseman
*Assistant Examiner* — Lucy Eppert
(74) *Attorney, Agent, or Firm* — Definitive Patents, member Synchrony IP; Timothy D. Snowden

(57) ABSTRACT

Apparatus and associated methods relate to a guidewire slack take-up module (STUM) that engages a guidewire, by a retractor module (RM), to displace the guidewire in a proximal direction (D1) in response to a tensioning command signal (TCS) and maintains a predetermined biasing force (PBF) in D1 when the RM is not engaged. In an illustrative example, the STUM may include a connection module (CM) disposed at a proximal end of a control member (CM). The CM may have its distal end fixedly attached to a distal end of a flexible shaft. The RM may, in response to the TCS, engage the CM to displace the proximal end of the CM in D1. A biasing member may apply the PBF to the CM in D1 when the RM is not engaging the CM. Various embodiments may advantageously reduce or eliminate slack in a guidewire of a steerable catheter.

20 Claims, 7 Drawing Sheets

(51) Int. Cl.
*A61M 25/01* (2006.01)
*A61M 25/09* (2006.01)

(52) U.S. Cl.
CPC .... *A61M 25/0116* (2013.01); *A61M 25/0147* (2013.01); *A61M 25/09* (2013.01); *A61B 2034/301* (2016.02); *A61B 2034/715* (2016.02); *A61M 2205/3553* (2013.01)

(58) Field of Classification Search
CPC ............... A61B 34/70; A61M 25/0116; A61M 25/0147; A61M 25/09; A61M 25/0136
See application file for complete search history.

(56) References Cited

U.S. PATENT DOCUMENTS

| | | | | |
|---|---|---|---|---|
| 5,626,595 | A | 5/1997 | Sklar et al. | |
| 5,634,936 | A | 6/1997 | Linden et al. | |
| 5,643,255 | A | 7/1997 | Organ | |
| 5,891,088 | A | 4/1999 | Thompson et al. | |
| 5,976,174 | A | 11/1999 | Ruiz | |
| 6,823,217 | B2 | 11/2004 | Rutten et al. | |
| 6,997,870 | B2 | 2/2006 | Couvillon, Jr. | |
| 7,386,203 | B2 | 6/2008 | Maitland et al. | |
| 7,850,642 | B2 | 12/2010 | Moll et al. | |
| 7,912,539 | B2 | 3/2011 | Doty et al. | |
| 7,931,616 | B2 | 4/2011 | Selkee | |
| 8,190,238 | B2 | 5/2012 | Moll et al. | |
| 8,202,244 | B2 | 6/2012 | Cohen et al. | |
| 8,262,694 | B2 | 9/2012 | Widomski et al. | |
| 8,882,786 | B2 | 11/2014 | Bearinger et al. | |
| 8,900,228 | B2 | 12/2014 | Grunewald et al. | |
| 8,956,304 | B2 | 2/2015 | Schecter | |
| 9,101,734 | B2 | 8/2015 | Selkee | |
| 9,220,433 | B2 | 12/2015 | Pitter et al. | |
| 9,295,551 | B2 | 3/2016 | Straubinger et al. | |
| 9,414,878 | B1 | 8/2016 | Wu et al. | |
| 9,629,989 | B2 | 4/2017 | Guillemot et al. | |
| 9,655,602 | B2 | 5/2017 | Ginn et al. | |
| 10,213,264 | B2 | 2/2019 | Tanner et al. | |
| 10,321,900 | B2 | 6/2019 | Au et al. | |
| 10,357,230 | B2 | 7/2019 | Bolduc | |
| 10,675,442 | B2 | 6/2020 | Douglas et al. | |
| 10,874,468 | B2 | 12/2020 | Wallace et al. | |
| 2002/0147462 | A1 | 10/2002 | Mair et al. | |
| 2005/0288706 | A1 | 12/2005 | Widomski et al. | |
| 2006/0052816 | A1 | 3/2006 | Bates et al. | |
| 2007/0103437 | A1 | 5/2007 | Rosenberg | |
| 2008/0214896 | A1 | 9/2008 | Krupa et al. | |
| 2008/0228104 | A1 | 9/2008 | Uber et al. | |
| 2008/0243064 | A1 | 10/2008 | Stahler et al. | |
| 2008/0255540 | A1 | 10/2008 | Selkee | |
| 2010/0079099 | A1* | 4/2010 | Katsuki | A61B 34/71 318/565 |
| 2010/0087804 | A1 | 4/2010 | Fridman et al. | |
| 2011/0028894 | A1 | 2/2011 | Foley et al. | |
| 2011/0060346 | A1 | 3/2011 | Jensen et al. | |
| 2011/0082497 | A1 | 4/2011 | DesLauriers et al. | |
| 2011/0130718 | A1 | 6/2011 | Kidd et al. | |
| 2012/0071752 | A1 | 3/2012 | Sewell et al. | |
| 2012/0143088 | A1 | 6/2012 | Schultz | |
| 2012/0179070 | A1 | 7/2012 | Pommer et al. | |
| 2012/0184955 | A1 | 7/2012 | Pivotto et al. | |
| 2012/0203142 | A1 | 8/2012 | Bedell | |
| 2013/0321262 | A1 | 12/2013 | Schecter | |
| 2014/0018732 | A1 | 1/2014 | Bagaoisan et al. | |
| 2014/0107427 | A1 | 4/2014 | Chow et al. | |
| 2014/0257327 | A1 | 9/2014 | Olson et al. | |
| 2014/0257333 | A1 | 9/2014 | Blumenkranz | |
| 2014/0276934 | A1 | 9/2014 | Balaji et al. | |
| 2014/0330309 | A1 | 11/2014 | Gonzalez et al. | |
| 2015/0073340 | A1 | 3/2015 | Pacheco et al. | |
| 2015/0090057 | A1 | 4/2015 | Pacheco et al. | |
| 2015/0153842 | A1 | 6/2015 | Obermeyer et al. | |
| 2015/0216553 | A1 | 8/2015 | Kessler et al. | |
| 2015/0297834 | A1 | 10/2015 | Buder et al. | |
| 2016/0000499 | A1 | 1/2016 | Lennox et al. | |
| 2016/0278841 | A1 | 9/2016 | Panescu et al. | |
| 2016/0288414 | A1 | 10/2016 | Ozbolat et al. | |
| 2016/0374719 | A1* | 12/2016 | Kessler | A61B 90/06 606/159 |
| 2017/0035434 | A1 | 2/2017 | Forbes | |
| 2017/0119484 | A1* | 5/2017 | Tanner | A61B 34/71 |
| 2017/0157361 | A1 | 6/2017 | Barrish et al. | |
| 2017/0360372 | A1 | 12/2017 | Hauck et al. | |
| 2018/0193007 | A1* | 7/2018 | Au | A61B 34/30 |
| 2018/0296285 | A1 | 10/2018 | Simi et al. | |
| 2018/0311006 | A1* | 11/2018 | Kose | A61B 34/74 |
| 2019/0192245 | A1* | 6/2019 | Abbott | A61B 34/37 |
| 2019/0357916 | A1 | 11/2019 | Inouye et al. | |
| 2020/0071550 | A1 | 3/2020 | Gaharwar et al. | |
| 2020/0324469 | A1 | 10/2020 | Zhang et al. | |

FOREIGN PATENT DOCUMENTS

| | | | |
|---|---|---|---|
| CN | 101918073 | B | 6/2014 |
| EP | 1594423 | A2 | 11/2005 |
| EP | 3175813 | A1 | 6/2017 |
| WO | 03088204 | A1 | 10/2003 |
| WO | 2011109283 | A1 | 9/2011 |
| WO | 2020014277 | A1 | 1/2020 |

OTHER PUBLICATIONS

A. Essop, "Scientists investigate directly 3D printing tissues within the body using robotics," 3D Printing Industry, Jun. 17, 2020. https://3dprintingindustry.com/news/scientists-investigate-directly-3dprinting-tissues-within-the-body-using-robotics-172637/ (accessed May 4, 2021).

C. Q. Choi, "3-D Printing inside the Body Could Patch Stomach Ulcers," Scientific American, Sep. 22, 2020, accessed May 4, 2021, https://www.scientificamerican.com/article/3-d-printing-inside-the-body-could-patch-stomachulcers/.

G. Ying et al., "An open-source handheld extruder loaded with pore-forming bioink for in situ wound dressing," Materials Today Bio, vol. 8, p. 100074, Sep. 2020, doi: 10.1016/j.mtbio.2020.100074, https://www.sciencedirect.com/science/article/pii/S259000642030034X.

International Preliminary Report on Patentability in related International Application No. PCT/US2022/070846, dated May 31, 2023, 34 pages.

International Search Report and Written Opinion of the International Searching Authority in related International Application No. PCT/US2022/070846, dated Jun. 3, 2022, 14 pages.

K. Ma et al., "Application of robotic-assisted in situ 3D printing in cartilage regeneration with HAMA hydrogel: An in vivo study," Journal of Advanced Research, vol. 23, pp. 123-132, May 2020, doi: 10.1016/j.jare.2020.01.010, https://www.sciencedirect.com/science/article/pii/S2090123220300102.

L. Gilbert, "Scientists use novel ink to 3D-print 'bone' with living cells," UNSW Newsroom, Jan. 25, 2021. https://newsroom.unsw.edu.au/news/health/scientists-use-novel-ink-3d-print-%E2%80%98bone%E2%80%99-living-cells-0 (accessed May 4, 2021).

R. Foresti et al., "In-vivo vascular application via ultra-fast bioprinting for future 5D personalised nanomedicine," Scientific Reports, vol. 10, No. 1, Art. No. 1, Feb. 2020, doi: 10.1038/s41598-020-60196-y.

V. Keriquel et al., "In situ printing of mesenchymal stromal cells, by laser-assisted bioprinting, for in vivo bone regeneration applications," Scientific Reports, vol. 7, No. 1, Art. No. 1, May 2017, doi: 10.1038/s41598-017-01914-x, https://www.nature.com/articles/s41598-020-60196-y.

W. Wei et al., "3D Printed Anchoring Sutures for Permanent Shaping of Tissues," Macromol Biosci, vol. 17, No. 12, Art. No. 12, Dec. 2017, doi: 10.1002/mabi.201700304.

W. Zhao and T. Xu, "Preliminary engineering for in situ in vivo bioprinting: a novel micro bioprinting platform for in situ in vivo

(56) References Cited

OTHER PUBLICATIONS bioprinting at a gastric wound site," Biofabrication, vol. 12, No. 4, Art. No. 4, Aug. 2020, doi: 10.1088/1758-5090/aba4ff.
Y. Chen et al., "Noninvasive in vivo 3D bioprinting," Science Advances, vol. 6, No. 23, Art. No. 23, Jun. 2020, doi: 10.1126/sciadv.aba7406, https://advances.sciencemag.org/content/6/23/eaba7406.
Filgueiras-Rama, D. and Merino, J., The Future of Pulmonary Vein Isolation, Arrythmia Electrophysiology Rev., Apr. 2013, p. 59-64, vol. 2(1), Radcliffe Card., UK.
Hansen Medical, Inc., Magellen Live Patient Case at TCT, Nov. 29, 2013 [online], [retrieved Jan. 27, 2017]. < URL: https://www.youtube.com/watch?v=vzf9AFndpcw>.
Okamura, A., Haptic Feedback in Robot-Assisted Minimally Invasive Surgery, Current Opinion in Urology, Jan. 2009, p. 102-107, vol. 19(1), Wolters Kluwer Health, Phil., PA.
Poty, H., et al., Robotic atrial fibrillation ablation . . . , Oct. 1, 2014, [online], [retrieved Jan. 27, 2017] <URL: https://www.youtube.com/watch?v=xPXHHCJ6icQ#t=261.7068103>.
Taylor, R. and Stoianovici, D., Medical Robotics in Computer-Integrated Surgery, IEEE Transactions on Robotics and Automation, Oct. 2003, p. 765-781, vol. 19 No. 5, IEEE, NY.

* cited by examiner

STEERABLE TIP CATHETER WITH AUTOMATIC TENSION APPARATUS

CROSS-REFERENCE TO RELATED APPLICATIONS

This application claims the benefit of U.S. Provisional Application Ser. No. 63/111,408, titled "Steerable Tip Catheter with Automatic Tension Apparatus," filed by John Pocrnich, et al., on Nov. 9, 2020.

This application incorporates the entire contents of the foregoing application(s) herein by reference.

The subject matter of this application may have common inventorship with and/or may be related to the subject matter of the following:

- U.S. Application Ser. No. 62/292,699, titled "Robotically Assisted Steerable Catheter," filed by Ryan J. Douglas, et al., on Feb. 8, 2016;
- U.S. application Ser. No. 15/425,982, titled "Robotically Augmented Catheter Manipulation Handle," filed by Ryan J. Douglas, et al., on Feb. 6, 2017, and issued as U.S. Pat. No. 10,675,442 on Jun. 9, 2020;
- U.S. application Ser. No. 16/861,633, titled "Robotically Augmented Catheter Manipulation Handle," filed by Ryan J. Douglas, et al., on Apr. 29, 2020;
- U.S. Application Ser. No. 63/154,192, titled "Steerable Sheath with Robotic Handle Stand," filed by John Swoyer, et al., on Feb. 26, 2021; and,
- U.S. application Ser. No. 17/305,856, titled "Systems and Methods for Minimally Invasive Delivery and In Vivo Creation of Biomaterial Structures," filed by John Swoyer, et al., on Jul. 15, 2021.

This application incorporates the entire contents of the foregoing application(s) herein by reference.

TECHNICAL FIELD

Various embodiments relate generally to steerable catheters.

BACKGROUND

Medical teams have available a wide variety of catheters, to enable provision of the right products for their patients' unique medical needs. For decades, with the help of catheters, medical teams have been able to drain fluids from body cavities, administer medications intravenously, perform surgical procedures and administer anesthetics, for example. As technology progressed, medical instrument designers provided modern medicine teams with guiding catheters and sheaths. Guiding catheters and sheaths are frequently used in many medical procedures due to their minimally invasive nature. For example, patients undergoing cardiac or other vascular procedures with guiding catheters and sheaths receive a minimally sized surgically-placed lumen (opening) to the skin.

Guiding catheters and sheaths, otherwise named "steerable" catheters and sheaths, may employ control wires that pass from the catheter interface through the catheter shaft and terminate at the catheter shaft tip. Tension applied to any of the control wires causes the catheter tip to deflect, giving control of orientation to the catheter tip, for example giving orientation control of the imaging angle of a tip mounted ultrasound transducer. This technology has made more advanced procedures possible using catheter-mounted instruments, benefiting patients with minimally invasive procedures, by entering a patient's body percutaneously or via natural orifices. Further descriptions that reference guided catheters may also apply to guided sheaths.

SUMMARY

Apparatus and associated methods relate to a guidewire slack take-up module (STUM) that engages a guidewire, by a retractor module (RM), to displace the guidewire in a proximal direction (D1) in response to a tensioning command signal (TCS) and maintains a predetermined biasing force (PBF) in D1 when the RM is not engaged. In an illustrative example, the STUM may include a connection module (CM) disposed at a proximal end of a control member (CM). The CM may have its distal end fixedly attached to a distal end of a flexible shaft. The RM may, in response to the TCS, engage the CM to displace the proximal end of the CM in D1. A biasing member may apply the PBF to the CM in D1 when the RM is not engaging the CM. Various embodiments may advantageously reduce or eliminate slack in a guidewire of a steerable catheter.

Various embodiments may achieve one or more advantages. For example, a biasing module may advantageously maintain a (predetermined) minimum tension in a corresponding control member. Accordingly, various embodiments may advantageously prevent slack in the corresponding control member.

In various embodiments, take-up of slack in a control member may advantageously increase accuracy of control of a steerable tip. Various embodiments may advantageously reduce or substantially eliminate 'slop' in operator controls by take-up of slack in the control members and/or maintaining a minimum biasing force to the control members during operation. Such embodiments may advantageously prevent unnecessary extension of actuation members. Various such embodiments may, for example, thereby reduce an amount of operation of the actuator(s) necessary to operate the steerable tip in a desired direction. Such embodiments may advantageously decrease procedure time. Some embodiments may, for example, advantageously increase patient safety (e.g., by increasing precision of tip control and/or reducing procedure time). Various embodiments may advantageously enable more precise procedures than are currently possible. Various embodiments may advantageously reduce cost associated with achieving an increased precision in tip control.

The details of various embodiments are set forth in the accompanying drawings and the description below. Other features and advantages will be apparent from the description and drawings, and from the claims.

BRIEF DESCRIPTION OF THE DRAWINGS

Like reference symbols in the various drawings indicate like elements.

DETAILED DESCRIPTION OF ILLUSTRATIVE EMBODIMENTS

To aid understanding, this document is organized as follows. First, to help introduce discussion of various embodiments, an exemplary slack take-up module (STUM) enabled catheter system is introduced with reference to FIGS. 1-2. Second, that introduction leads into a description with reference to FIGS. 3-5 of some exemplary embodiments of STUMs. Third, with reference to FIGS. 6-8, exemplary STUMs are described in application to exemplary steerable catheter systems. Fourth, with reference to FIGS. 9-10, the discussion turns to exemplary embodiments that illustrate operation of various STUM embodiments. Finally, the document discusses further embodiments, exemplary applications and aspects relating to STUMs.

Figure 1:
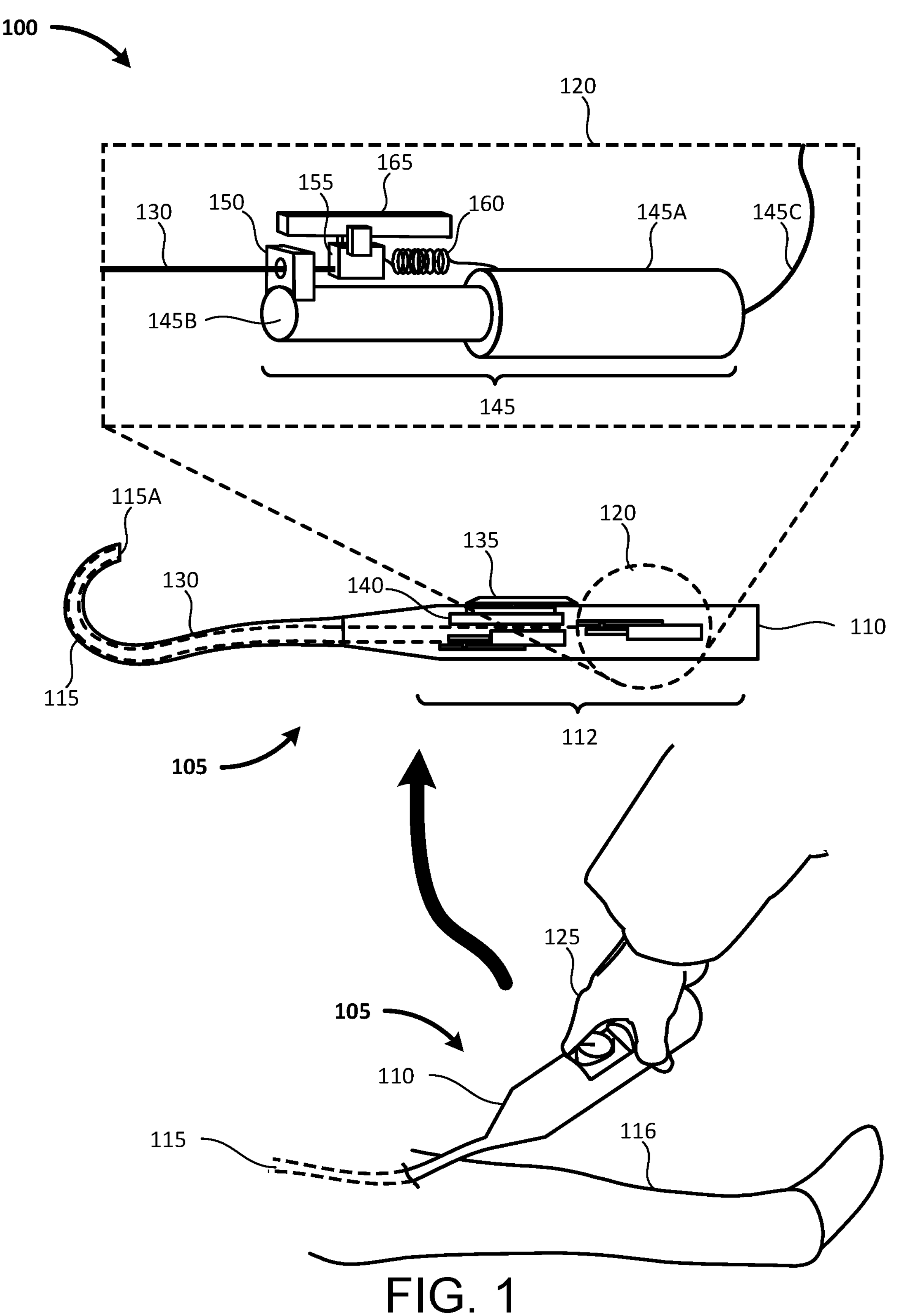
FIG. 1 depicts an exemplary slack take-up module (STUM) employed in an illustrative use-case scenario.

FIG. 1 depicts an exemplary slack take-up module (STUM) employed in an illustrative use-case scenario. In an exemplary scenario 100, a catheter system 105 includes a body 110 and a steerable catheter 115. As depicted, the steerable catheter 115 is passed into a patient 116 (e.g., via a vein) by a healthcare provider 125 (e.g., a physician) operating the body 110.

The body 110 of the catheter system 105 includes a control system 112. The control system 112 includes a STUM 120. As depicted, two STUM 120 units are included in the control system 112. In the depicted example, each STUM 120 is operably coupled to a control member 130. The control member 130 is operably coupled (e.g., fixedly coupled) to a steerable tip 115A at a distal end of the steerable catheter 115. Each STUM 120 may operate the corresponding control member 130 to control a deflection of the steerable tip 115A.

In the depicted example, the control system 112 is configured such that each STUM 120 independently selectively actuates corresponding control member 130. An input interface 135 is operably coupled to a control unit 140. Operation of the input interface 135 may be translated by the control unit 140 to generate tensioning command signal(s). The control unit 140 may be operably coupled to (each of) the STUM 120 to transmit the tensioning command signal(s) the STUM 120 in response to operation of the input interface 135. For example, the input interface 135 may be operated by the healthcare provider 125 by rotating the input interface 135 (depicted as a knob in this exemplary illustration). The input from the healthcare provider 125 may correspond to a command to deflect the steerable tip 115A in a first direction (e.g., in a plane defined by the two depicted control members 130). The control unit 140 may generate a tensioning command signal based on the input (signal) from the input interface 135 configured to cause actuation of the STUMs 120 to effect the input from the healthcare provider 125. The control unit 140 may apply the tensioning command signal (s) to at least one STUM 120 to actuate the corresponding control member 130 and cause deflection of the steerable tip 115A.

In the exemplary scenario 100, the STUM 120 includes an actuator 145. The actuator 145 includes an actuator module 145A configured to operate an actuation member 145B. As depicted, the actuator 145 includes a conduit 145C. The conduit 145C may, for example, include an electrical conduit (e.g., cable, cord, wire). The conduit 145C may, for example, conduct data to and/or from the actuator module 145A. The conduit 145C may, for example, conduct power to and/or from the actuator module 145A.

An engagement module 150 is coupled to a distal end of the actuation member 145B. For example, the engagement module 150 may be fixedly coupled to the distal end of the actuation member 145B. The engagement module 150 is configured to slidingly engage the corresponding control member 130 corresponding to the STUM 120 via a connector module 155. As depicted, the corresponding control member 130 passes through the engagement module 150 via an aperture (e.g., a hole through the engagement module 150). Motion of the engagement module 150 along a path defined by the corresponding control member 130 may, by way of example and not limitation, apply minimal or substantially no force to the corresponding control member 130. Retraction of the actuation member 145B (e.g., by operation of the actuator module 145A) may not cause retraction of the corresponding control member 130 (e.g., corresponding to a rightward motion in the exemplary scenario 100) until the engagement module 150 engages the connector module 155. Continued retraction of the actuation member 145B may then cause the engagement module 150 to displace the connector module 155, thereby applying a tension to the corresponding control member 130. The tension applied may, for example, induce retraction of the corresponding control member 130.

The connector module 155 may, for example, include a ferrule coupled to (a proximal end of) the corresponding control member 130. The corresponding control member 130 may, for example, be implemented as a guidewire.

The connector module 155 is coupled to a biasing module 160. The biasing module 160 is coupled, in the depicted example, to the actuator module 145A. In various embodiments, by way of example and not limitation, the biasing module 160 may be coupled to a (fixed) point and/or structure other than the actuator module 145A. The biasing module 160 may apply a biasing force to the proximal end of the corresponding control member 130 such that a (predetermined) minimum tension is always applied to the corresponding control member 130. For example, when the actuation member 145B is extended such that the engagement module 150 disengages the connector module 155 (e.g., sliding over the corresponding control member 130 while applying tension at least below a predetermined minimum biasing force applied by the biasing module 160), then the biasing module 160 may advantageously maintain a (predetermined) minimum tension in the corresponding control member 130. Accordingly, various embodiments may advantageously prevent slack in a corresponding control member 130.

In various embodiments, take-up of slack in a control member may advantageously increase accuracy of control of a steerable tip. For example, if an operator of a steerable catheter steers the tip one way, causing a first level of tension to be applied to a corresponding control member, an opposing control member may go slack. Accordingly, if an opposing force (e.g., pressure of tissue against the steerable tip) changes (e.g., reduces) as the operator manipulates the steerable catheter, the steerable tip may deflect out of an intended and/or desired position and/or orientation. If the operation applies an input to steer the tip in an opposing direction, the operator may have to apply an unexpected and/or unknown amount of input to first cause slack to be taken out of the opposing control member before the steerable tip begins to respond. Various embodiments may advantageously reduce or substantially eliminate 'slop' in the operator controls by take-up of slack in the control members and/or maintaining a minimum biasing force to the control members during operation. Such embodiments may advantageously prevent unnecessary extension of actuation members. Various such embodiments may, for example, thereby reduce an amount of operation of the actuator(s) necessary to operate the steerable tip in a desired direction.

In the exemplary scenario 100, the STUM 120 includes a guide module 165. As depicted, the connector module 155 is slidingly coupled to the guide module 165. For example, the guide module 165 may define a predetermined motion profile (e.g., path of travel, range of travel) for the connector module 155. In some embodiments the guide module 165 may include at least one sensor. For example, the guide module 165 may include a position and/or displacement sensor. The sensor(s) may detect a position of the connector module 155. The sensor(s) may, for example, be operably coupled to provide feedback based on a position and/or motion of the connector module 155. In some embodiments the sensor(s) may be operably coupled to provide feedback to the actuator 145. In some embodiments the sensor(s) may, for example, be operably coupled to provide feedback to the control unit 140. In some embodiments, feedback to the healthcare provider 125 may, for example, be generated in response to a signal(s) from the sensor(s). In some embodiments a controller (e.g., the control unit 140) may operate the actuator module 145A according to the feedback from the sensor(s).

In some embodiments the sensor(s) may include a linear encoder (e.g., optical, magnetic). In some embodiments the sensor(s) may include a rotary encoder. In some embodiments the sensor may, for example, include a rack and pinion. Motion of the connector module 155 relative to the guide module 165 may cause rotation of the pinion. A rotation sensor may determine rotation (e.g., speed, revolution count) of the pinion.

Figure 2:
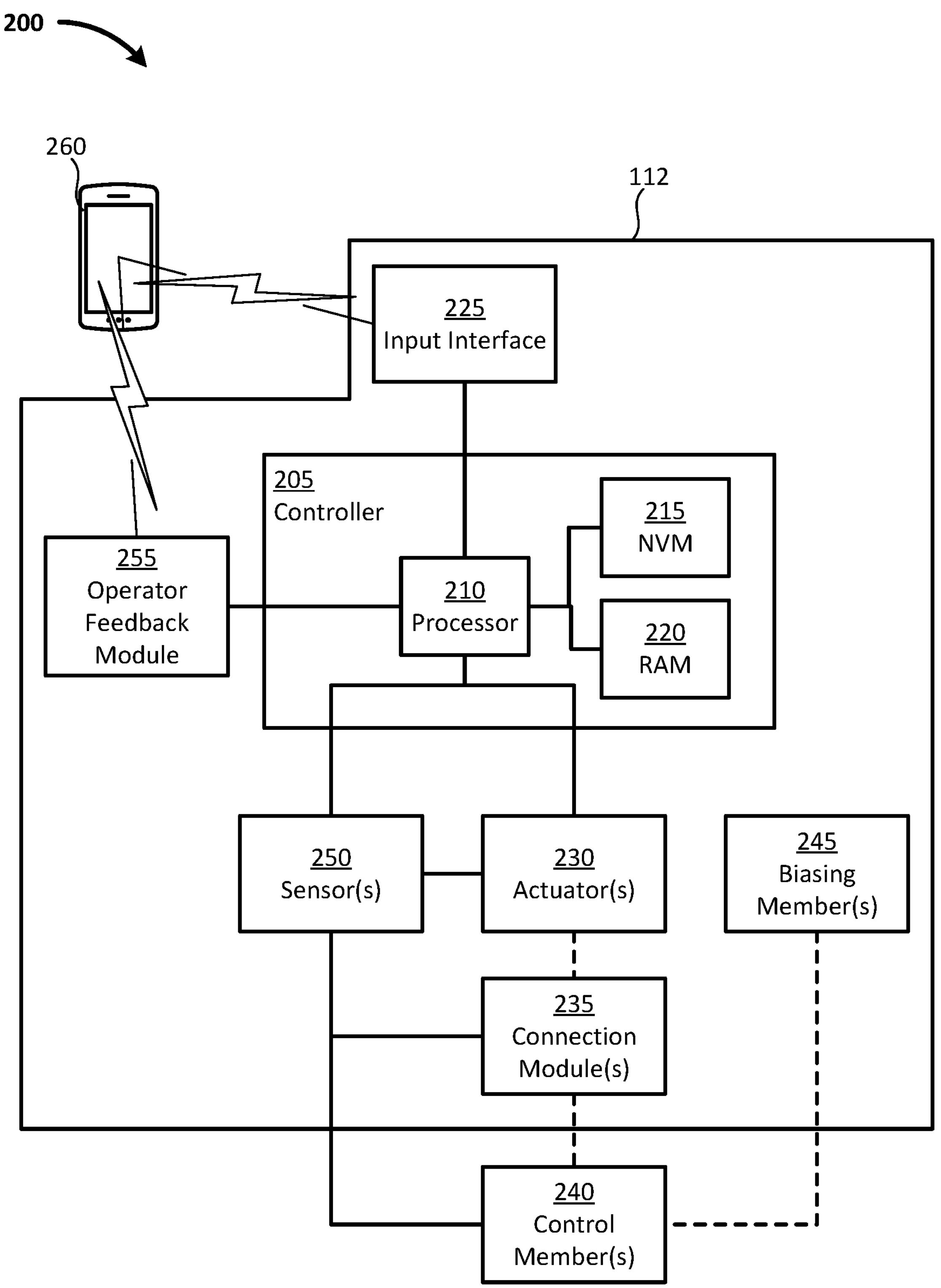
FIG. 2 depicts a block diagram of an exemplary STUM.

FIG. 2 depicts a block diagram of an exemplary STUM. A robotic catheter system 200 includes a control system 112. The control system 112 includes a controller 205. In some embodiments the controller 205 may include integrated circuit(s). As depicted, the controller 205 includes a processor 210. In some embodiments, the processor 210 may include one or more processors. The processor 210 is operably coupled to a random-access memory module (a RAM 220). In some embodiments the RAM 220 may include one or more RAM modules. The processor 210 is operably coupled to a non-volatile memory module (an NVM 215). In some embodiments the NVM 215 may include one or more NVM modules. In various embodiments, at least one program of instructions may be stored on the NVM 215 and/or the RAM 220. The program(s) of instructions may, for example, be executed by the processor 210 to cause operations (e.g., control member retraction, slack take-up, control member release, tensioning command generation) to be performed by the control system 112. In some embodiments, the controller 205 may, by way of example and not limitation, be configured as disclosed at least with reference to the control unit 140.

The processor 210 is operably coupled to an input interface 225. The input interface 225 may, for example, be configured as disclosed at least with reference to the input interface 135. The input interface 225 may, for example, receive input from an operator. The input interface 225 may, for example, receive mechanical input (e.g., manipulation by an operator) directly from an operator. The input interface 225 may, for example, receive mechanical input indirectly (e.g., via a robotic interface) from an operator. In some embodiments the input interface 225 may, for example, receive input electronically (e.g., via a remote control manipulated by an operator). The input interface 225 may, for example, be connected to a command source via a wired connection. The input interface 225 may, for example, be connected to a command source via a wireless connection.

The processor 210 is operably coupled to an actuator 230. In some embodiments the actuator 230 may, for example, include multiple actuators. Each actuator 230 may, for example, be independently controlled by the controller 205. The actuator 230 is operably coupled to a connection module 235 of a control member 240. Operation of the actuator 230 in response to a signal(s) from the processor 210 may, for example, cause the actuator 230 to engage the connection module 235 (e.g., via an engagement module coupled to the actuator). The connection module 235 is coupled to (selectively) engage a control member 240. In the depicted example, the dashed lines may, for example, represent mechanical connections. For example, the actuator 230 may be configured such as the actuator 145 as disclosed at least with reference to FIG. 1. The connection module 235 may, for example, be configured as disclosed at least with reference to the connector module 155. The control member 240 may, for example, be configured as disclosed at least with reference to corresponding control member 130.

In the depicted example, the control system 112 may be configured to independently control each of multiple control members 240. For example, in response to a signal(s) generated by the input interface 225 in response to operator input, the controller 205 may generate a tensioning command signal(s) as a function of the input signal(s). The controller 205 may selectively operate the actuator(s) 230 to selectively and independently control retraction (e.g., via controlling a tensile force applied) of multiple control members 240 via the connection module 235.

A biasing member 245 is coupled to the control member 240. The biasing member 245 may apply a predetermined minimum force (e.g., tension) to the control member 240. For example, when the actuator 230 is not active and/or is extended such that a force applied to the control member 240 by the actuator 230 (via the connection module 235) is less than the predetermined minimum force, than the biasing member 245 may be configured to maintain the predetermined minimum force on the control member 240. In some embodiments the predetermined minimum force may, for example, be fixed. In some embodiments the predetermined minimum force may, for example, be adjustable. As an illustrative example, the minimum force may be manually adjustable. The minimum force may, in some embodiments, by way of example and not limitation, be adjustable by an actuator, such as in response to an adjustment command from the controller 205. The adjustment command may, for example, be received from an operator. The adjustment command may, for example, be generated automatically. For example, the adjustment command may be automatically generated in response to a signal from a sensor 250 indicating slack in the control member 240.

In the depicted example, the sensor 250 is operably coupled to the connection module 235. The sensor 250 is operably coupled, as depicted, to the control member 240. As depicted, the sensor 250 is operably coupled to the actuator 230. In some embodiments the sensor 250 may be coupled to the connection module 235 or the control member 240. In some embodiments the sensor 250 may be omitted. The sensor 250 may, for example, be configured such as disclosed at least with reference to the exemplary sensor(s) of the guide module 165 in FIG. 1. In some embodiments the sensor 250 may include multiple sensors.

For example, in some embodiments a sensor 250 may be configured to detect position. For example, a sensor 250 may be configured to detect a location of the control member, actuator, and/or connection module. In some embodiments a sensor 250 may, for example, be configured to detect a speed and/or velocity of motion (e.g., of the control member, the actuator, the connection module). In some embodiments a sensor 250 may, for example, be configured to detect displacement. For example, a sensor 250 may be configured to detect displacement of the connection module.

In various embodiments a sensor 250 may be configured to detect force and/or pressure. For example, a sensor 250 may be configured to detect force and/or pressure on the control member 240. In some embodiments a sensor 250 may, for example, be configured to detect force and/or pressure on the biasing member 245. In some embodiments a sensor 250 may be configured to detect force and/or pressure on the actuator 230.

In the depicted example, the control system 112 includes an operator feedback module 255 operably coupled to the processor 210. As depicted, the operator feedback module 255 is communicably coupled to a mobile interface 260. As depicted, the mobile interface 260 is a smartphone. For example, the operator feedback module 255 may generate and/or transmit feedback (e.g., generated by the controller 205 in response to signal(s) from the sensor 250, the actuator 230, and/or the input interface 225) to the mobile interface 260. As depicted, the mobile interface 260 may be communicably coupled to the input interface 225. For example, the mobile interface 260 may be operated to transmit signals corresponding to the operator input to the input interface 225.

Figure 3:
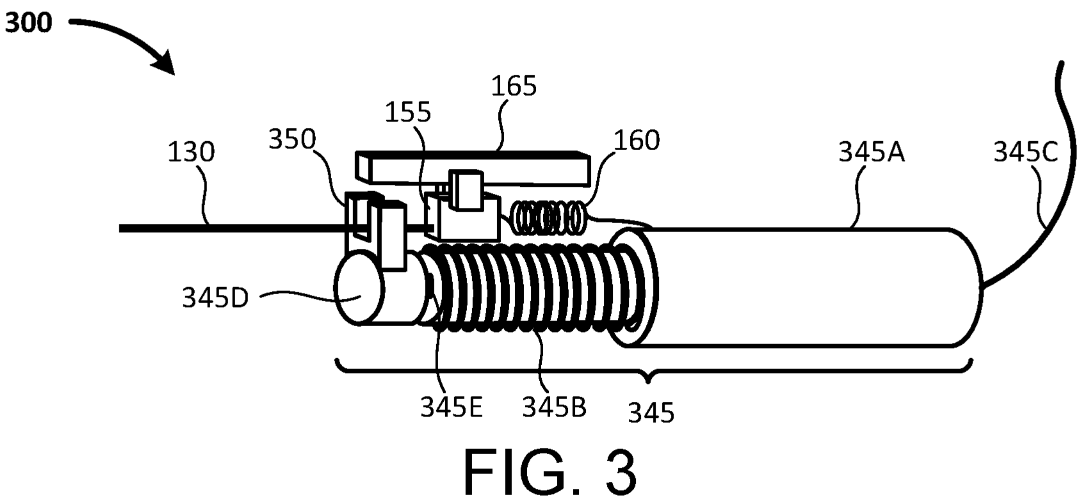
FIG. 3 depicts an exemplary STUM with a threaded actuator.

FIG. 3 depicts an exemplary STUM with a threaded actuator. A STUM 300 includes an actuator 345. The actuator 345 includes an actuator module 345A coupled to and configured to operate an actuation member 345B. The actuator module 345A is coupled to a conduit 345C. In the depicted example, the actuation member 345B is rotatably coupled to an end module 345D by a swivel joint 345E. The end module 345D is (fixedly) coupled to an engagement module 350.

In the depicted example, the actuation member 345B is threaded. For example, the actuator module 345A may include a rotary actuator (e.g., rotating motor) configured to rotate the actuation member 345B. The threads of the actuation member 345B may, for example, engage corresponding threaded features (not shown) in the actuator module 345A such that the rotary motion is converted to axial motion advancing or retracting the actuation member 345B with respect to the actuator module 345A. In some embodiments, by way of example and not limitation, the actuator module 345A may include a stepper motor. In some embodiments the actuator module 345A may, for example, include a servo motor.

The engagement module 350 engages the corresponding control member 130. As depicted, the engagement module 350 includes a slot which the corresponding control member 130 passes through. Accordingly, for example, the engagement module 350 may advance and/or retract along a longitudinal axis of the actuator 345. The swivel joint 345E may allow the end module 345D to remain coupled to the corresponding control member 130 during rotation of the actuation member 345B. Accordingly, rotation of the actuation member 345B may be translated into advancement and/or retraction of the engagement module 350. The actuator 345 may be operated such that the engagement module 350 selectively engages the connector module 155.

Figure 4:
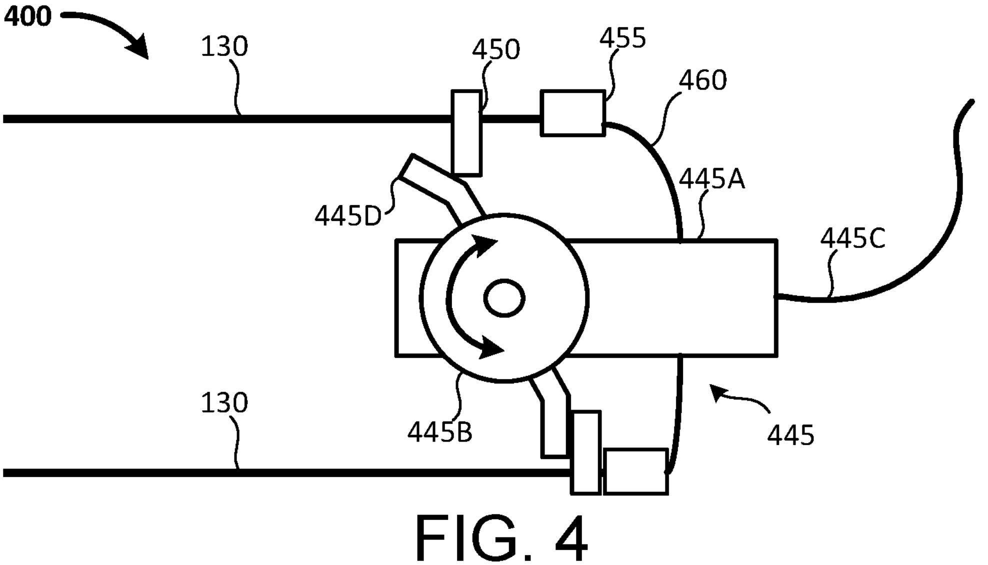
FIG. 4 depicts an exemplary dual-STUM with a rotary actuator.

FIG. 4 depicts an exemplary dual-STUM with a rotary actuator. A STUM 400 is operably coupled to selectively retract control members 130. An actuator 445 includes an actuator module 445A. The actuator module 445A is operably coupled to a rotary actuator 445B. In the depicted example, the actuator module 445A is operably coupled to a conduit 445C. In some embodiments the 445C may, for example, transmit data and/or power. In some embodiments the 445C may, for example, be omitted. For example, in some embodiments the actuator module 445A may operate the 445B in response to a tensioning command signal (e.g., via the [no text] 445C. In some embodiments the rotary actuator 445B may be mechanically coupled to an input interface. In some embodiments the rotary actuator 445B may also be configured as an input interface. Operation of the rotary actuator 445B to induce rotation about an axis of rotation passing through a center of the rotary actuator 445B may induce motion of actuation arms 445D.

The actuation arms 445D are operably coupled to the rotary actuator 445B. For example, in some embodiments the actuation arms 445D may be directly coupled to the rotary actuator 445B. In some embodiments the actuation arms 445D may, for example, be coupled by a linkage assembly to the rotary actuator 445B (e.g., a gear system such as a planetary gear system). Motion of the actuation arms 445D may cause the actuation arms 445D to displace an engagement module 450. The engagement module 450 may be configured to slide relative to the corresponding control member 130. Proximal (e.g., to the right in the illustration) displacement of the engagement module 450 may cause the engagement module 450 to engage a connection module 455. The connection module 455, as depicted, is (fixedly) coupled to the corresponding control member 130. Accordingly, proximal displacement of the engagement module 450 may, for example, cause rearward displacement of the connection module 455, thereby inducing retraction of the corresponding control member 130.

As depicted, each connection module 455 is coupled to a biasing member 460. The biasing member 460 may, for example, include a (flat) spring member. As an exemplary illustration, the biasing member 460 may include spring steel. The biasing member 460, in the depicted example, couples the connection module 455 to the actuator module 445A. In some embodiments the biasing member 460 may couple the connection module 455 to another (fixed) point. The biasing member 460 may, for example, maintain a (predetermined) minimum force on the corresponding control member 130. As depicted, in the lower corresponding control member 130, displacement of the engagement module 450 such that the corresponding control member 130 is retracted may reduce deflection of the biasing member 460 (e.g., reducing tension applied by the biasing member 460 to the connection module 455). The STUM 400 may, for example, advantageously provide a compact mechanical implementation of slack take-up with selective actuation of the control members 130.

In some embodiments the actuation arms 445D may, for example, be independently operable. For example, each arm may be on a separate rotational collar. The collar may, for example, be independently engaged by the rotary actuator 445B. In some embodiments each arm may, for example, be coupled to an independently controlled (rotary) motor (e.g., stepper, servo).

Figure 5:
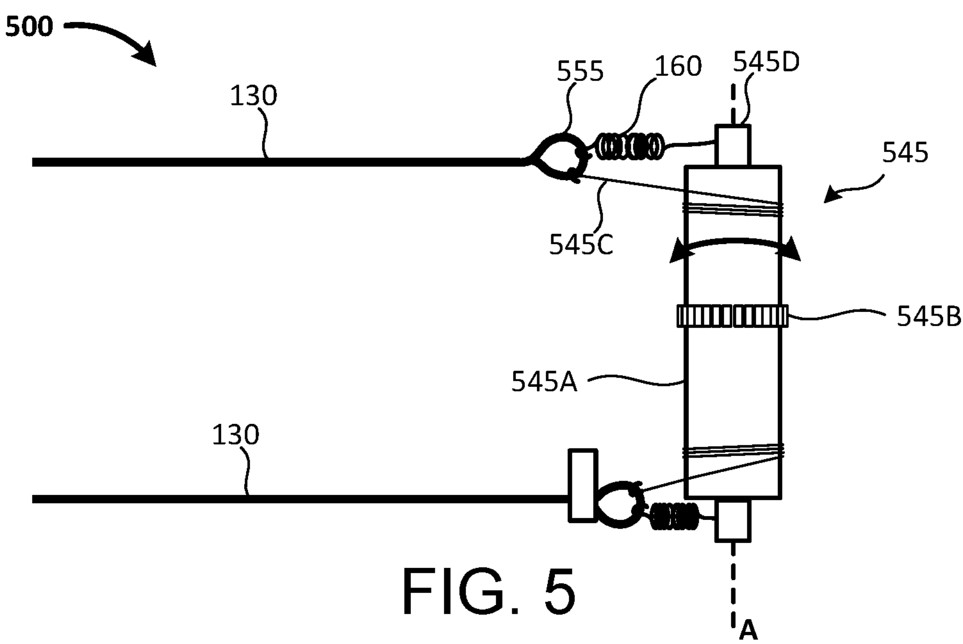
FIG. 5 depicts an exemplary dual-STUM with a rotary drum actuator.

FIG. 5 depicts an exemplary dual-STUM with a rotary drum actuator. A STUM 500 includes. An actuator 545 includes an actuator body 545A. The actuator body 545A is provided with an engagement module 545B. The engagement module 545B, as depicted, includes a ring of teeth around a circumference of the actuator body 545A. The teeth may, for example, be configured to be driven by a corresponding driving gear (e.g., ring gear, spur gear, worm gear). The driving gear (not shown) may, for example, be operated by a user (e.g., a thumb of the user) to generate a tensioning command signal via mechanical engagement with the engagement module 545B. In some embodiments the driving gear may, for example, be automatically operated in response to a user input signal.

The actuator body 545A is provided with an engagement member 545C corresponding to each control member 130. As depicted, the 545C is configured as a flexible member (e.g., cable, wire, cord) wrapped around the actuator body 545A. The actuator body 545A may, for example, be configured as a generally cylindrical drum configured to be rotated about an axis A. For example, the actuator body 545A may rotate about a shaft 545D. The engagement member 545C is coupled to the corresponding control member 130 via a connector module 555. As depicted, the connector module 555 is configured as a loop formed in a proximal end of the control member 130.

The biasing module 160 is coupled to the connector module 555 and to the shaft 545D. Accordingly, the biasing module 160 may advantageously apply a (predetermined) minimum force to the corresponding control member 130 via the connector module 555.

In some embodiments, a first portion of the actuator body 545A corresponding to the lower corresponding control member 130 may, for example, be independently rotatable and/or controllable relative to a second portion of the actuator body 545A corresponding to the upper corresponding control member 130. In some embodiments, for example, each corresponding control member 130 may be independently controlled by the actuator 545.

Figure 6:
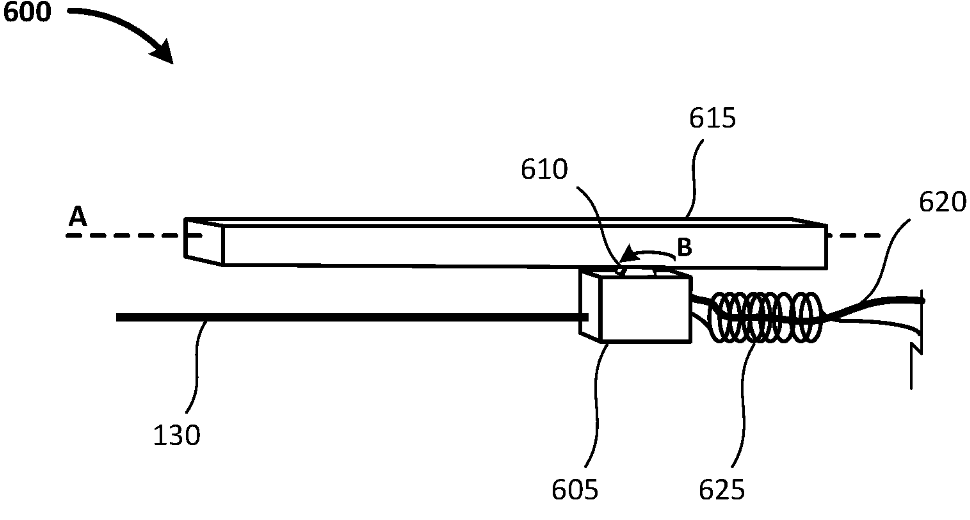
FIG. 6 depicts an exemplary STUM having a selectively driven rotating member engaging a linear member.

FIG. 6 depicts an exemplary STUM having a selectively driven rotating member engaging a linear member. A STUM 600 may include an actuator 605. The actuator 605 may include a wheel 610. For example, the wheel 610 may be a pinion. The wheel 610 may engage a linear member 615. The linear member may, for example, include a rack. Operation of the actuator 605 may, for example, induce rotation of the wheel 610. Rotation of the wheel 610 may cause translation of the actuator 605 relative to the linear member 615 (e.g., by teeth of the wheel 610 engaging corresponding features of the linear member 615). The actuator 605 is coupled to the control member 130. Accordingly, linear translation of the 605 along the axis A may induce retraction of the corresponding control member 130. The actuator 605 may, for example, receive and/or transmit data and/or power through a conduit 620.

In various embodiments the actuator 605 may, by way of example and not limitation, only be driven in a proximal direction (e.g., to the right in the illustration). In some embodiments, for example, activation of the actuator 605 may induce rotation of the wheel 610 in a first rotational direction B. Rotation of the wheel 610 in the first rotational direction may induce proximal displacement of the actuator 605 along the axis A, thereby inducing retraction of the control member 130. Deactivation of the actuator 605 may, for example, cease rotation of the wheel 610 by the actuator 605. A tension in the control member 130 (e.g., due to a force applied to a corresponding steerable tip) may cause the actuator 605 to be displaced distally in the absence of being driven by rotation of the wheel 610. In some embodiments the wheel 610 may 'free-wheel' as the actuator 605 is displaced distally by tension in the control member 130.

As depicted, a biasing member 625 is coupled to the actuator 605. A proximal end of the biasing member 625 may, for example, be anchored to a fixed structure. In some embodiments the biasing member 625 may, by way of example and not limitation, be anchored to the linear member 615. The biasing member 625 may be configured to maintain application of a (predetermined) minimum force to the control member 130. For example, as the corresponding control member 130 displaces the actuator 605 distally, extension of the biasing member 625 may increase a force applied to the actuator 605 by the biasing member 625. Once a force applied by the biasing member 625 ($T_B$) exceeds a force applied by the corresponding control member 130 ($T_C$), such that $T_B>T_C$, then the actuator 605 may stop. Accordingly, a predetermined minimum tension may be applied by the biasing member 625. Such embodiments may advantageously prevent slack in the control member 130. When the wheel 610 is driven again by the actuator 605 (e.g., in response to a tensioning command signal), then the actuator 605 may advantageously (substantially) immediately apply tension to the control member 130 without first having to take out slack in the control member 130.

In some embodiments the actuator 605 may, for example, not be directly coupled to the 130. The corresponding control member 130 may, for example, slidingly pass through and/or around the actuator 605. In some embodiments, the actuator 605 may, for example, selectively engage a connection module (not shown) coupled to (a proximal end) of the corresponding control member 130.

Figures 7, 8, 9:
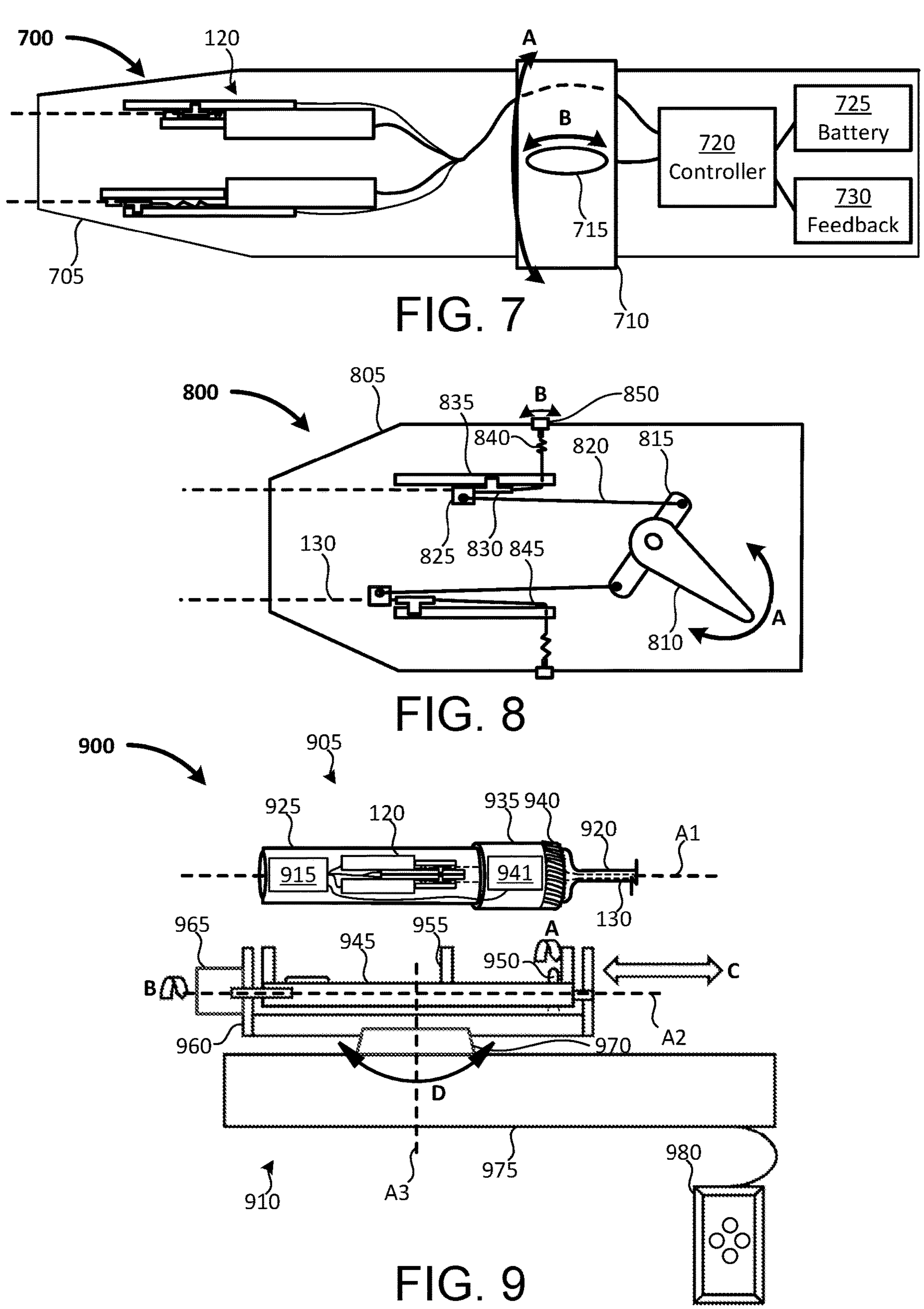
FIG. 7 depicts an exemplary catheter body with electronically actuated STUMs.
FIG. 8 depicts an exemplary catheter body with manually actuated STUMs.
FIG. 9 depicts an exemplary selectively robotically manipulated catheter with electronically actuated STUMs.

FIG. 7 depicts an exemplary catheter body with electronically actuated STUMs. A robotic catheter 700 includes a body 705. A first input interface 710 is disposed externally to the body 705. As depicted, the first input interface 710 is a collar disposed around the body 705 and rotatable about the body 705. For example, an operator may rotate the 710 in either rotational direction A about the body 705. The first input interface 710 is provided with a second input interface 715. As depicted, the second input interface 715 is configured as a wheel rotatably coupled to the first input interface 710. The second input interface 715 may be rotated in either rotational direction B, such as, for example, by an operator (e.g., by a thumb). In some embodiments, the first input interface 710 and/or the second input interface 715 may be provide with a neutral position (e.g., corresponding to no input). The first input interface 710 and/or second input interface 715 may be configured to automatically return to the corresponding neutral position upon cessation of input from an operator.

In the depicted example, the first input interface 710 and/or the second input interface 715 is operably coupled to a controller 720. The controller 720 may, for example, be configured as disclosed at least with reference to the controller 205. The controller 720 is operably coupled to an energy storage module (battery 725) and a feedback unit 730. In some embodiments the feedback unit 730 may, for example, be omitted. The controller 720 is further operably coupled to a pair of STUM 120. Operation of the first input interface 710 and/or second input interface 715 may generate an input signal(s) corresponding to a desired deflection of a steerable tip. In response to the input signal(s), the controller 720 may generate a tensioning command signal(s) as a function of the input signal(s) and/or sensor signal(s) from the STUM 120. Actuator(s) of the STUM 120 may (independently) operate one or more the STUM 120 to selectively and independently retract a corresponding control member.

In various embodiments, the feedback unit 730 may, for example, generate feedback in response to signal(s) received from the STUM(s) 120. For example, the feedback unit 730 may generate signals configured to generate visual and/or audio feedback (e.g., on a display module (not shown), on a mobile computing device screen). In some embodiments the feedback unit 730 may generate haptic feedback (e.g., through the body 705, the first input interface 710, and/or the second input interface 715). The feedback unit 730 may, for example, generate feedback in response to a level of force required to maintain a commanded position. For example, resistance to deflection from a neutral position(s) may be increased in the first input interface 710 and/or second input interface 715 in response to an increased force applied by a STUM 120 to achieve a commanded deflection. Accordingly, the robotic catheter 700 may advantageously provide feedback to an operator of conditions at a steerable tip of the catheter (e.g., tissue changes) that the operator may not otherwise readily be able to feel while operating the robotic catheter 700.

FIG. 8 depicts an exemplary catheter body with manually actuated STUMs. A robotic catheter system 800 includes a body 805. The body 805 is provided with an input interface 810. The input interface 810, as depicted is configured as a lever rotatably coupled (e.g., mounted) to the body 805. The input interface 810 may, for example, be operated by a user to rotate the 810 in either rotational direction A.

The input interface 810 is coupled to a lever arm 815. A (mechanical) input signal generated by the input interface 810 induces a corresponding rotation of the lever arm 815. In some embodiments, by way of example and not limitation, the lever arm 815 may be directly and/or fixedly mechanically coupled to the input interface 810. The lever arm 815 is operably coupled to proximal ends of a pair of linking members 820. As depicted, each linking member 820 is configured as a (rigid) linear member (e.g., rod). Each linking member 820 is coupled at a proximal end to an engagement module 825. In some embodiments, the engagement module 825 may, for example, be configured with respect to a corresponding control member 130 as disclosed at least with reference to the engagement module 150.

Rotation of the lever arm 815 may displace a first (upper in the illustration) linking member 820 proximally and a second (lower in the illustration) linking member 820 distally. Proximal displacement of a linking member 820 may cause the engagement module 825 to displace a connection module 830 in a proximal direction along a path defined by a linear member 835 (e.g., guide rail, linear scale). The connection module 830 is coupled to a proximal end of a corresponding control member 130. Accordingly, proximal displacement of the connection module 830 may retract the corresponding control member 130 in a proximal direction.

Distal displacement of a linking member 820 may cause the engagement module 825 displace in a distal direction. The corresponding engagement module 825 may slide over and/or by the corresponding control member 130 such that the corresponding control member 130 is not proximally displaced in response. The connection module 830 is coupled to a biasing member 840. In the depicted example, by way of example and not limitation, the biasing member 840 passes over a friction-reduction member 845 (e.g., bearing surface, roller) and through the linear member 835. The biasing member 840 is anchored, as depicted, at an opposite end to the body 805 by an adjustment module 850. The adjustment module 850 may, for example, be operated by a user to adjust a (predetermined) minimum force applied by the biasing member 840 to the corresponding control member 130 via the engagement module 825. For example, the adjustment module 850 may be provided with threads and may engage threads in the body 805 to adjust a pre-load applied to the biasing member 840. A user may operate the adjustment module 850 to rotate in a rotational direction B to reduce or increase the pre-load to the biasing member 840.

FIG. 9 depicts an exemplary selectively robotically manipulated catheter with electronically actuated STUMs. In a robotic steerable catheter system 900, a body 905 of a handheld catheter system is configured to be removably mounted to a robotic conduit steering module 910. The robotic conduit steering module 910 may, for example, include a controller 915 (e.g., such as the controller 205), (independently and) selectively controllable STUMs 120, one or more communication modules, or some combination thereof.

The body 905 includes a control module 935. The control module 935 is provided with a steering element 940. The control module 935 may, for example, be operably coupled to control an orientation and/or geometry of a steerable catheter 920. For example, as depicted, the control module 935 may be configured as an input interface. An input module 941 may generate an input signal in response to operation of the control module 935. For example, the input module 941 may generate an input signal(s) in response to rotation of the control module 935 relative to the body 905 about a longitudinal axis A1. The controller 915 may generate a tensioning command signal(s) in response to the input signal(s). The STUMs 120 may selectively and independently operate in response to the tensioning command signal(s) such that the corresponding control member 130 are selectively and independently retracted to induce a desired deflection in the steerable catheter 920.

The robotic conduit steering module 910 is provided with a carriage 945 configured to receive the body 905. An actuation element 950 may be configured to releasably engage the steering element 940. For example, the actuation element 950 may rotate (e.g., driven by an actuator such as an electric motor). The carriage 945 includes a coupling member 955 which may be configured to releasably couple to the body 905 (e.g., behind the control module 935). Accordingly, the body 905 may be releasably axially and rotationally coupled to the carriage 945.

The control module 935 may be rotatable about A1 relative to the body 905 and the carriage 945. The steering element 940 may be held engaged against the actuation element 950. A pattern on the steering element 940 may, for example, be complementary to a pattern (not shown) on the actuation element 950. The actuation element 950 may rotate, as shown by motion "A" (e.g., in response to a command from an operator), thereby inducing rotation about A1 of the control module 935 via the steering element 940 (e.g., having a gear-tooth pattern). Accordingly, the control module 935 may rotate relative to the body 905, thereby inducing a (desired) deflection in the steerable catheter 920. A steerable tip (e.g., a distal end) of the steerable catheter 920 may thereby be advantageously controlled.

The carriage 945 may be rotatably coupled to a frame 960. For example, the carriage 945 may be configured to rotate (motion "B") relative to the frame 960 about a longitudinal axis A2 of the carriage 945. A carriage actuator 965 is operably coupled to the carriage 945 such that operation of the carriage actuator 965 may induce rotation of the frame 960 about the longitudinal axis of the carriage 945. The carriage actuator 965 may, for example, be an actuator. The carriage 945 may, for example, be operated by a controller (e.g., in response to commands of an operator). Accordingly, (controlled) rotation of the body 905 may be advantageously induced about A2 when the body 905 is releasably coupled to the carriage 945.

The frame 960 is coupled to an upper base 970. For example, the frame 960 may be slidably and/or rotatably coupled to the upper base 970. An actuator (not shown) may be configured to advance and/or retract the frame 960 along A2 relative to the upper base 970 (motion "C"), to rotate the frame 960 about an axis A3 relative to the upper base 970 (motion "D"), or some combination thereof.

The upper base 970 is coupled to a lower base 975. The upper base 970 may, for example, be rotatably and/or slidably coupled to the lower base 975. An actuator (not shown) may be configured to advance and/or retract the upper base 970 along A2 relative to the lower base 975 (motion "C"), to rotate the lower base 975 about A3 relative to the lower base 975 (motion "D"), or some combination thereof.

In some embodiments, for example, the frame 960 may rotate about A3 relative to the upper base 970 and the upper base 970 may translate along A2 relative to the lower base 975. In some embodiments, for example, the frame 960 may translate along A2 relative to the upper base 970 and the upper base 970 may rotate about A3 relative to the lower base 975.

The lower base 975 is operably coupled to a human machine interface 980. As depicted, the human machine interface 980 is in wired electrical communication with the lower base 975. The human machine interface 980 may, for example, be coupled to the robotic catheter system 200 (e.g., the controller 205). The human machine interface 980 may, for example, be coupled to the controller 205 via the input interface 225.

In such embodiments, the human machine interface 980 may, by way of example and not limitation, be wirelessly coupled to the controller 205 (e.g., in the robotic conduit steering module 910). The human machine interface 980 may, for example, be a dedicated HMI. The human machine interface 980 may, for example, be a multipurpose HMI (e.g., a mobile computing device). In some embodiments, the human machine interface 980 may, for example, include a visual feedback (e.g., a display screen), tactile (e.g., haptic) feedback mechanism(s), or some combination thereof. The human machine interface 980 may, for example, transduce (mechanical) inputs from a user into signals provided to the controller 205. The controller 205 may, for example, generate signals to operate the various actuators (e.g., actuator (s) of the STUMs 120, carriage actuator 965, actuator of the actuation element 950, actuator of the frame 960, actuator of the upper base 970, actuator of the drive module 925). Accordingly, an operator (e.g., a physician) may advantageously operate the body 905 via the human machine interface 980.

Accordingly, various embodiments may advantageously provide multiple (e.g., 2, 3) degrees of freedom of the body 905 (e.g., motion B, C, and D). Various embodiments may advantageously operate the steerable catheter 920 along at least one additional degree of freedom (e.g., 2, 3 degrees of freedom). Accordingly, (robotic) control of the body 905 may advantageously provide (precise) control over a steerable catheter 920 and associated steerable tip.

Figure 10:
FIG. 10 depicts an exemplary method of STUM operation.
Figure 10:
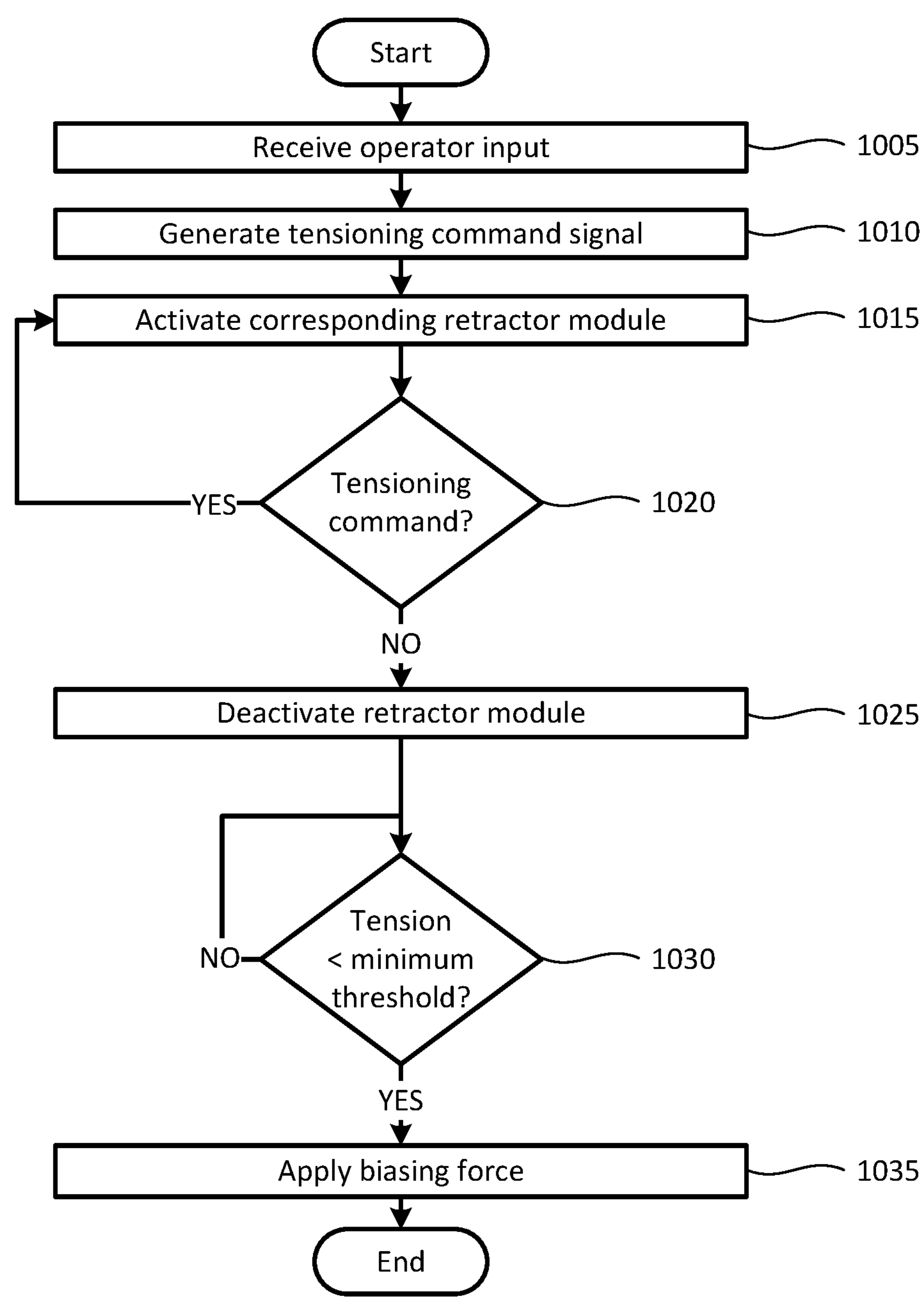

FIG. 10 depicts an exemplary method of STUM operation. In a method 1000, operator input is received in a step 1005. An input signal(s) may be generated from the operator input. A tensioning command signal(s) is generated, in a step 1010, based on the operator input. For example, the tensioning command signal may be a mechanical signal transmitted by mechanical linkage(s). In some embodiments the tensioning command signal may, for example, be electronic. In some embodiments the tensioning command signal may include pneumatic signal(s). In some embodiments the tensioning command signal may include hydraulic signal(s). In some embodiments the tensioning command signal may include magnetic signal(s).

At least one retractor module is activated, in a step 1015, in response to the tensioning command signal(s). For example, a STUM may be operated (e.g., electrically, mechanically) to engage a connection module and retract a control member. If the tensioning command is determined, in a decision point 1020, to still be received and/or a new tensioning command is received, then the method 1000 returns to the step 1015. Otherwise, the retractor module is deactivated, in a step 1025. Once the tension (e.g., in the control member) is determined to be below a predetermined minimum threshold, in a decision point 1030, then a biasing force is applied in a step 1035 and the method 1000 ends. The method 1000 may, for example, be iteratively applied.

In some embodiments, the method 1000 may be configured, by way of example and not limitation, to be entirely mechanically applied in response to manual operation of an input interface by an operator. In some embodiments, at least some steps of the method 1000 may be configured, for example, to be dynamically and/or automatically applied by at least one controller in response to operator input. For example, at least some portion of the method 1000 may be tangibly embodied as a program of instructions stored on a memory module(s) and executed by at least one processor.

Figure 11:
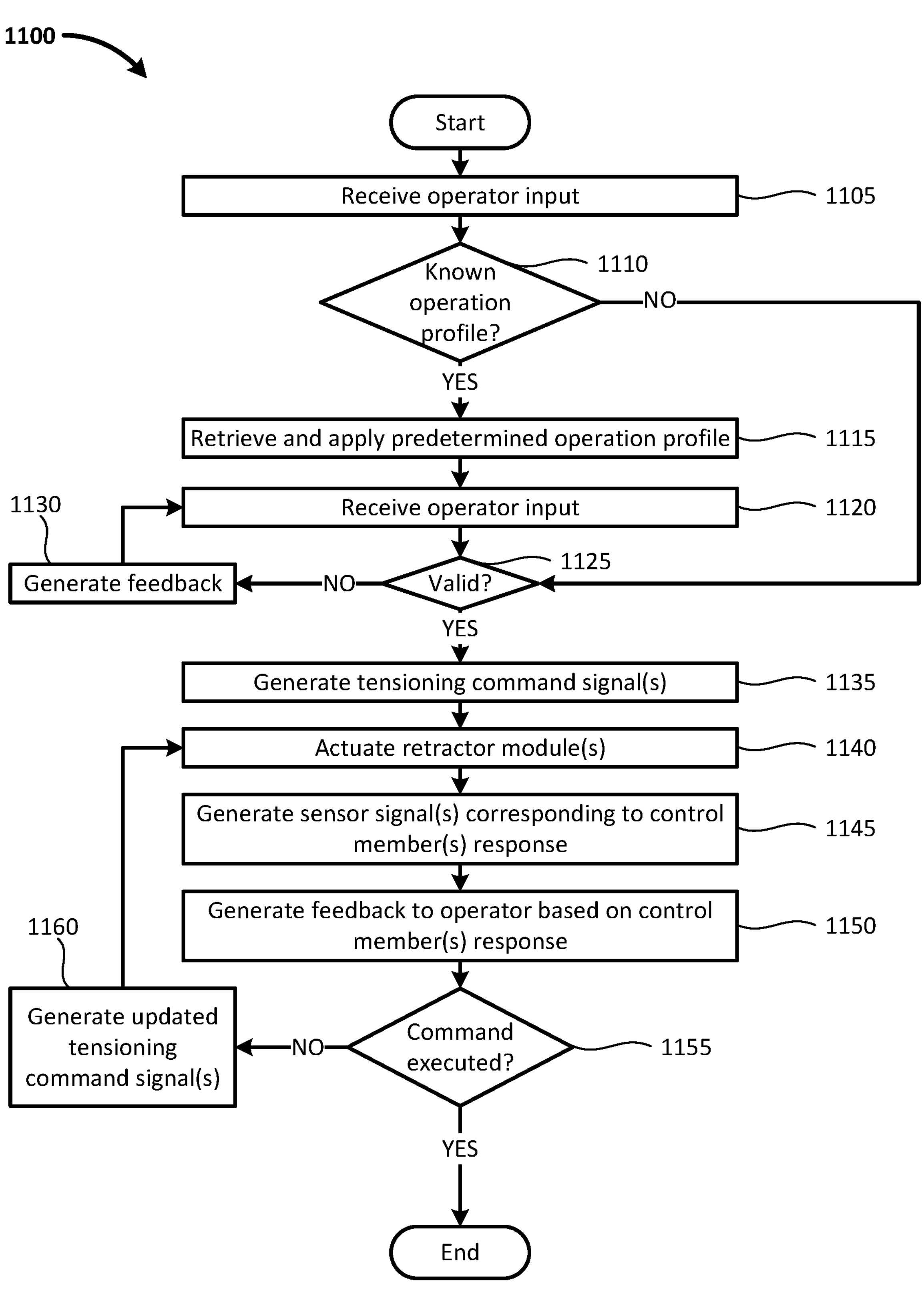
FIG. 11 depicts an exemplary method of STUM operation with predetermined operation parameters and operational feedback.

FIG. 11 depicts an exemplary method of STUM operation with predetermined operation parameters and operational feedback. In a method 1100, operator input is received in a step 1105. If a known operation profile is found, in a decision point 1110, corresponding to the operator input, then the (predetermined) operation profile is retrieved in a step 1115 and applied. For example, the operator input may correspond to a predetermined procedure type. The operator input may, for example, correspond to a predetermined tissue type and/or operating environment (e.g., skeletal muscle tissue, vasculature, esophagus). In some embodiments, for example, an operator may initiate a robotic catheter system with pre-operation settings by making one or more selections. In some embodiments the operator input may be made through an interface (e.g., graphical user interface) on the catheter system. In some embodiments the operator input may be uploaded (e.g., via a portable data storage device). In some embodiments the operator input may be transmitted to a controller from a medical control and/or records system.

In some embodiments, an operation profile may be provided via the operator input. In some embodiments the operation profile may be located in a local and/or remote storage module(s) and be identified based on operator input. In some embodiments, the operation profile may be dynamically generated based on operator input. In some embodiments, a profile may correspond to a device (e.g., the catheter system, a connected catheter system, connected accessories, the STUM).

Application of the profile may include, for example, setting one or more criteria in the threshold. For example, a predetermined minimum force may be defined by the profile. Force and/or speed of actuator(s) of STUM(s) may, for example, be defined by the profile. In some embodiments, operation of one or more connected actuator(s) may be determined (e.g., releasably coupled accessories). In some embodiments, interaction with one or more sensor(s) may, for example, be defined by the profile.

Further operator input is received in a step 1120. For example, the operator may begin operating the robotic catheter system to perform a procedure. The procedure may, for example, correspond to the operation profile applied in the step 1115. The operator input may, for example, correspond to a commanded deflection of a steerable tip. In some embodiments the operator input may, for example, correspond to a commanded rotation of a catheter (e.g., about a longitudinal axis of a catheter handle body). If the operator input is determined to be valid, in a decision point 1125, then a corresponding tensioning command signal is generated in a step 1135. If the operator input is determined to not be valid, in the decision point 1125, then feedback is generated in a step 1130 and the method 1100 returns to the step 1120. The input may be determined to not be valid, for example, if the input would violate predetermined ranges (e.g., force applied, displacement induced, available range of motion). In some embodiments, the decision point 1125 and/or the 1130/may, for example, be omitted.

In response to the tensioning command signal(s) generated (e.g., by a controller such as the controller 205) in the step 1135, at least one retractor module is actuated in a step 1140. As an illustrative example with reference to FIG. 1, the retractor module may, by way of example and not limitation, correspond to the actuator 145. If a sensor(s) is available (e.g., and activated such as according to a predetermined operation profile) a sensor signal(s) is generated in a step 1145 corresponding to the response of the control member. Feedback is generated, in a step 1150, based on the control member(s) response. The feedback may, for example, be generated based on the sensor signal(s). In some embodiments the step 1150 may, for example, be omitted.

If the operator command is determined to be (fully) executed, in a decision point 1155, then the method 1100 ends. For example, the operator command may be determined to be executed once the retractor module is actuated according to the tensioning command signal(s) in the step 1135. The operator command may be determined to be (fully) executed based on the sensor signal(s) generated in the step 1145 (e.g., and received by the controller(s)). If the operator command is determined to not be executed, in the decision point 1155, then an updated tensioning command signal(s) is generated in a step 1160 and the method 1100 returns to the step 1140.

As an illustrative example, an operator command may correspond to the operator input in the step 1120. A first tensioning command signal may be generated, and the retractor module(s) actuated accordingly. Sensor signal(s) may be generated based on the response of the control modules to the actuation of the retractor module(s). An updated tensioning command signal (e.g., to correct an over-actuation, to overcome an under-actuation) may be generated based on the sensor signal(s). For example, a feedback loop (e.g., servo loop) controlled by at least one processor may automatically implement an operator input.

For example, the method 1100 may be tangibly embodied as a program of instructions stored on a memory module(s) and executed by at least one processor.

Although various embodiments have been described with reference to the figures, other embodiments are possible. For example, although various embodiments depict a pair of STUM, various embodiments may include a single STUM. An opposing control member may, for example, be coupled to a biasing member. In some embodiments, more than two STUMs may be used. At least one STUM may, by way of example and not limitation, be provided for each control member. Some such embodiments may, for example, have four control members (e.g., control of the steerable tip in two directions), and so may have four STUMs. Some embodiments may, for example, have three control members (e.g., in a generally triangular configured to provide substantially 360-degree deflection control of a steerable tip). Such embodiments may, for example, have three STUMs (e.g., a STUM corresponding to each control member).

In some embodiments, for example, a biasing member may include an extension spring. In some embodiments a biasing member may, for example, include a compression spring. In some embodiments a biasing member may include an actuator. The actuator may, for example, be powered. The actuator may, for example, be automatically controlled.

In some embodiments, for example, a force applied by a biasing member may be defined by Equation 1 (e.g., when the biasing member includes a spring):

$$F = k \cdot x, \quad \text{Equation 1:}$$

where F is the biasing force applied by the biasing member, k is a constant (e.g., a spring constant), and x is a distance of displacement of the spring. In some embodiments, k may be selected and/or modified to achieve a predetermined minimum force. In some embodiments x may be (dynamically) adjusted to reach a desired predetermined minimum force.

Although an exemplary system has been described with reference to the figures, other implementations may be deployed in other industrial, scientific, medical, commercial, and/or residential applications.

In various embodiments, some bypass circuits implementations may be controlled in response to signals from analog or digital components, which may be discrete, integrated, or a combination of each. Some embodiments may include programmed, programmable devices, or some combination thereof (e.g., PLAs, PLDs, ASICs, microcontroller, microprocessor), and may include one or more data stores (e.g., cell, register, block, page) that provide single or multi-level digital data storage capability, and which may be volatile, non-volatile, or some combination thereof. Some control functions may be implemented in hardware, software, firmware, or a combination of any of them.

Computer program products may contain a set of instructions that, when executed by a processor device, cause the processor to perform prescribed functions. These functions may be performed in conjunction with controlled devices in operable communication with the processor. Computer program products, which may include software, may be stored in a data store tangibly embedded on a storage medium, such as an electronic, magnetic, or rotating storage device, and may be fixed or removable (e.g., hard disk, floppy disk, thumb drive, CD, DVD).

Although an example of a system, which may be portable, has been described with reference to the above figures, other implementations may be deployed in other processing applications, such as desktop and networked environments.

Temporary auxiliary energy inputs may be received, for example, from chargeable or single use batteries, which may enable use in portable or remote applications. Some embodiments may operate with other DC voltage sources, such as batteries, for example. Alternating current (AC) inputs, which may be provided, for example from a 50/60 Hz power port, or from a portable electric generator, may be received via a rectifier and appropriate scaling. Provision for AC (e.g., sine wave, square wave, triangular wave) inputs may include a line frequency transformer to provide voltage step-up, voltage step-down, and/or isolation.

Although particular features of an architecture have been described, other features may be incorporated to improve performance. For example, caching (e.g., L1, L2, . . . ) techniques may be used. Random access memory may be included, for example, to provide scratch pad memory and or to load executable code or parameter information stored for use during runtime operations. Other hardware and software may be provided to perform operations, such as network or other communications using one or more protocols, wireless (e.g., infrared) communications, stored operational energy and power supplies (e.g., batteries), switching and/or linear power supply circuits, software maintenance (e.g., self-test, upgrades), and the like. One or more communication interfaces may be provided in support of data storage and related operations.

Some systems may be implemented as a computer system that can be used with various implementations. For example, various implementations may include digital circuitry, analog circuitry, computer hardware, firmware, software, or combinations thereof. Apparatus can be implemented in a computer program product tangibly embodied in an information carrier, e.g., in a machine-readable storage device, for execution by a programmable processor; and methods can be performed by a programmable processor executing a program of instructions to perform functions of various embodiments by operating on input data and generating an output. Various embodiments can be implemented advantageously in one or more computer programs that are executable on a programmable system including at least one programmable processor coupled to receive data and instructions from, and to transmit data and instructions to, a data storage system, at least one input device, and/or at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, which may include a single processor or one of multiple processors of any kind of computer. Generally, a processor will receive instructions and data from a read-only memory or a random-access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including, by way of example, semiconductor memory devices, such as EPROM, EEPROM, and flash memory devices; magnetic disks, such as internal hard disks and removable disks; magneto-optical disks; and CD-ROM and DVD-ROM disks. The processor and the memory can be supplemented by, or incorporated in, ASICs (application-specific integrated circuits).

In some implementations, each system may be programmed with the same or similar information and/or initialized with substantially identical information stored in volatile and/or non-volatile memory. For example, one data interface may be configured to perform auto configuration, auto download, and/or auto update functions when coupled to an appropriate host device, such as a desktop computer or a server.

In some implementations, one or more user-interface features may be custom configured to perform specific functions. Various embodiments may be implemented in a computer system that includes a graphical user interface and/or an Internet browser. To provide for interaction with a user, some implementations may be implemented on a computer having a display device, such as a CRT (cathode ray tube) or LCD (liquid crystal display) monitor for displaying information to the user, a keyboard, and a pointing device, such as a mouse or a trackball by which the user can provide input to the computer.

In various implementations, the system may communicate using suitable communication methods, equipment, and techniques. For example, the system may communicate with compatible devices (e.g., devices capable of transferring data to and/or from the system) using point-to-point communication in which a message is transported directly from the source to the receiver over a dedicated physical link (e.g., fiber optic link, point-to-point wiring, daisy-chain). The components of the system may exchange information by any form or medium of analog or digital data communication, including packet-based messages on a communication network. Examples of communication networks include, e.g., a LAN (local area network), a WAN (wide area network), MAN (metropolitan area network), wireless and/or optical networks, the computers and networks forming the Internet, or some combination thereof. Other implementations may transport messages by broadcasting to all or substantially all devices that are coupled together by a communication network, for example, by using omni-directional radio frequency (RF) signals. Still other implementations may transport messages characterized by high directivity, such as RF signals transmitted using directional (i.e., narrow beam) antennas or infrared signals that may optionally be used with focusing optics. Still other implementations are possible using appropriate interfaces and protocols such as, by way of example and not intended to be limiting, USB 2.0, Firewire, ATA/IDE, RS-232, RS-422, RS-485, 802.11 a/b/g, Wi-Fi, Ethernet, IrDA, FDDI (fiber distributed data interface), token-ring networks, multiplexing techniques based on frequency, time, or code division, or some combination thereof. Some implementations may optionally incorporate features such as error checking and correction (ECC) for data integrity, or security measures, such as encryption (e.g., WEP) and password protection.

In various embodiments, the computer system may include Internet of Things (IoT) devices. IoT devices may include objects embedded with electronics, software, sensors, actuators, and network connectivity which enable these objects to collect and exchange data. IoT devices may be in-use with wired or wireless devices by sending data through an interface to another device. IoT devices may collect useful data and then autonomously flow the data between other devices.

Various examples of modules may be implemented using circuitry, including various electronic hardware. By way of example and not limitation, the hardware may include transistors, resistors, capacitors, switches, integrated circuits, other modules, or some combination thereof. In various examples, the modules may include analog logic, digital logic, discrete components, traces and/or memory circuits fabricated on a silicon substrate including various integrated circuits (e.g., FPGAs, ASICs), or some combination thereof. In some embodiments, the module(s) may involve execution of preprogrammed instructions, software executed by a processor, or some combination thereof. For example, various modules may involve both hardware and software.

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. A robotic catheter system comprising:
- a body extending along a longitudinal axis and comprising an input interface;
- a steerable catheter extending distally from the body;
- a control member extending from the body along a curvilinear path and anchored to a distal region of the steerable catheter, the control member is configured to deflect a distal tip of the steerable catheter at least in a first plane parallel to the longitudinal axis;
- a control member slack take-up module (CMSTUM) operably coupled to the body and the control member, the CMSTUM comprising:
  - a connector module disposed at a proximal end of the control member;
  - an engagement module configured to be selectively moved into and out of engagement with the connector module;
  - a retractor module configured to move the engagement module to contact and engage the connector module, in response to receiving a tensioning command signal generated in response to operation of the input interface, such that the proximal end of the control member is displaced in a proximal direction; and,
  - a biasing member that applies a predetermined biasing force to the connector module in a proximal direction when the engagement module is not engaging and separated from the connector module.

2. The robotic catheter system of claim 1, further comprising a second control member and a second CMSTUM operably coupled to the body and the second control member,
- wherein, in response to the tensioning command signal, the CMSTUM and the second CMSTUM are engaged such that one of the control member and the second control member are retracted by the corresponding retractor module, and the other of the control member and the second control member is correspondingly disengaged by the corresponding retractor module, such that the distal tip of the steerable catheter is deflected in the first plane.

3. The robotic catheter system of claim 1, further comprising:
- a second control member and a second CMSTUM operably coupled to the body and the second control member; and,
- a third control member and a third CMSTUM operably coupled to the body and the third control member,
- wherein, in response to the tensioning command signal, at least the CMSTUM, the second CMSTUM, and the third CMSTUM selectively operate the corresponding control members such that the distal tip of the steerable catheter is deflected in a second plane out of the first plane and substantially parallel to the longitudinal axis.

4. The robotic catheter system of claim 1, wherein the input interface comprises a mechanical member disposed on the body and configured to be operated by a user such that the tensioning command signal is generated in response the operation of the mechanical member.

5. The robotic catheter system of claim 1, wherein the input interface is configured to receive wireless input signals such that the tensioning command signal is generated in response to the wireless input signals.

6. The robotic catheter system of claim 1, wherein the input interface is configured to receive input from a remotely controlled cradle when the body is coupled to the remotely controlled cradle.

7. A guidewire slack take-up module comprising:
- a connector module disposed at a proximal end of a control member extending along a curvilinear path, the control member having its distal end fixedly attached to a distal end of a flexible shaft;
- an engagement module configured to be selectively moved into and out of engagement with the connector module;
- a retractor module, configured to move the engagement module to contact and engage the connector module in response to receiving a tensioning command signal such that the proximal end of the control member is displaced in a proximal direction; and,
- a biasing member that applies a predetermined biasing force to the connector module in a proximal direction when the engagement module is not engaging and is separated from the connector module.

8. The guidewire slack take-up module of claim 7, wherein, in an absence of a second tensioning command signal, the retractor module is configured to disengage the connector module upon completion of engagement of the connector module in response to the tensioning command signal.

9. The guidewire slack take-up module of claim 7, wherein the control member comprises a guidewire.

10. The guidewire slack take-up module of claim 7, wherein the connector module comprises a ferrule fixedly coupled to the control member.

11. The guidewire slack take-up module of claim 7, wherein the biasing member comprises at least one spring module.

12. The guidewire slack take-up module of claim 7, wherein the tensioning command signal comprises a mechanical signal which operates the retractor module in response to operation of an input interface.

13. The guidewire slack take-up module of claim 7, wherein:
- the tensioning command signal comprises an electrical signal generated in response to operation of an input interface,
- the retractor module comprises an actuator configured to selectively displace the connector module, and,
- the input interface is operably coupled to the actuator such that the actuator operates to displace the connector module in response to the electrical signal.

14. The guidewire slack take-up module of claim 7, further comprising a feedback module operably coupled to generate a position feedback signal as a function of a position of the connector module.

15. The guidewire slack take-up module of claim 14, further comprising a control module operably coupled to the retractor module and operably coupled to the feedback module, wherein the control module generates the tensioning command signal based on an input command received in response to operation of an input interface and based on the position feedback signal.

16. The guidewire slack take-up module of claim 7, further comprising a feedback module configured to generate a force feedback signal as a function of a force applied to the connector module.

17. The guidewire slack take-up module of claim 7, wherein the predetermined biasing force is adjustable.

18. The guidewire slack take-up module of claim 7, wherein the retractor module comprises a linear actuator.

19. The guidewire slack take-up module of claim 7, wherein the retractor module comprises a rotating actuator.

20. A guidewire slack take-up module comprising:

a control member extending along a curvilinear path, the control member having its distal end fixedly attached to a distal end of a flexible shaft;

means for selectively engaging a proximal end of the control member, in response to a tensioning command signal, to displace the proximal end of the control member in a proximal direction; and, means for applying a predetermined biasing force to the control member in a proximal direction when the means for selectively engaging is not engaging and separated from the proximal end of the control member.

* * * * *